(12) United States Patent
Jaeger

(10) Patent No.: US 7,192,745 B2
(45) Date of Patent: Mar. 20, 2007

(54) METHOD FOR THE DETERMINATION OF A NUCLEIC ACID USING A CONTROL

(75) Inventor: Stephan Jaeger, Penzberg (DE)

(73) Assignee: Roche Molecular Systems, Inc., Alameda, CA (US)

(*) Notice: Subject to any disclaimer, the term of this patent is extended or adjusted under 35 U.S.C. 154(b) by 0 days.

(21) Appl. No.: 10/087,631

(22) Filed: Mar. 1, 2002

(65) Prior Publication Data

US 2003/0054372 A1    Mar. 20, 2003

(30) Foreign Application Priority Data

Mar. 2, 2001 (EP) .................................. 01105172

(51) Int. Cl.
*C12P 19/34* (2006.01)
*C07H 21/04* (2006.01)

(52) U.S. Cl. ................. 435/91.2; 536/24.33; 536/23.1; 435/91.1

(58) Field of Classification Search ............... 536/23.1, 536/24.32, 24.3, 24.33; 435/6, 91.1, 810, 435/91.2

See application file for complete search history.

(56) References Cited

U.S. PATENT DOCUMENTS

| | | | |
|---|---|---|---|
| 4,458,066 A | 7/1984 | Caruthers et al. | 536/27 |
| 4,683,202 A * | 7/1987 | Mullis | 435/91 |
| 5,344,757 A | 9/1994 | Holtke et al. | 435/6 |
| 5,474,796 A | 12/1995 | Brennan | 427/2.13 |
| 5,702,888 A | 12/1997 | Holtke et al. | 435/6 |
| 5,770,360 A | 6/1998 | Kievits et al. | 435/6 |
| 5,837,442 A * | 11/1998 | Tsang | 435/5 |
| 5,837,501 A | 11/1998 | Beumer et al. | 435/91.2 |
| 5,840,487 A * | 11/1998 | Nadeau et al. | 435/5 |
| 6,147,199 A | 11/2000 | Seela et al. | 536/23.1 |
| 6,211,158 B1 | 4/2001 | Seela et al. | 514/44 |
| 2001/0006800 A1 | 7/2001 | Walkerpeach et al. | 435/91.1 |

FOREIGN PATENT DOCUMENTS

| | | |
|---|---|---|
| EP | 0 286 028 B1 | 3/1988 |
| EP | 0 324 474 B1 | 1/1989 |
| EP | 0 476 014 B1 | 3/1994 |
| EP | 0 680 969 A2 | 4/1995 |
| EP | 0 624 161 B1 | 2/1999 |
| EP | 01 10 5172 | 1/2002 |
| WO | WO 92/02638 | 2/1992 |
| WO | WO 92/20702 | 11/1992 |
| WO | WO 00/29613 A1 | 5/2000 |

OTHER PUBLICATIONS

Gagnor et al. Nucleic acid Research, vol. 17, No. 13, pp. 5107-5114, 1989.*

(Continued)

*Primary Examiner*—Kenneth R. Horlick
*Assistant Examiner*—Cynthia Wilder
(74) *Attorney, Agent, or Firm*—Townsend and Townsend and Crew LLP

(57) ABSTRACT

The present invention is directed to a method for the determination of a target nucleic acid using a special control nucleic acid, a method for the amplification of a partial sequence of said target nucleic acid using primers, a special control and a kit containing said control. The sequence of these control nucleic acids are at least in part parallel-complementary to the sequence of the target nucleic. These controls have similar properties as the target nucleic acid in hybridization and amplification methods, but can be well differentiated from the target nucleic acid by their different sequence.

14 Claims, 5 Drawing Sheets

OTHER PUBLICATIONS

Gagnor et al. Nucleic acids Research, vol. 15, No. 24, pp. 10419-10436,, 1987.*

Bolli et al. Nucleic acids Research, vol. 24, No. 13, pp. 4665-4672, 1996.*

Ahern, H. The Scientist. vol. 15, No. 9, pp. 20-24, Jul. 1995.*

Weller et al. Applied and Environmental Microbiology, vol. 66, No. 7, pp. 2853-2858, Jul. 2000.*

Tchurikov et al. Federation of European Biochemical Societies, vol. 297, No. 3, pp. 233-236, Feb. 1992.*

Melton et al. Nucleic acids Research, vol. 12, No. 18, pates 7035-7056, 1984.*

Fukui, et al, 1978, "XLIV. Synthesis and Properties of Poly(2-Azaadenylic Acid) and Poly(2-Azainosinic Acid)*", *Biochimica et Biophysica Acta*, 520:441-451.

Hoheisel, J., 1996, "Sequence-independent and linear variation of oligonucleotide DNA binding stablities", *Nucleic Acids Research*, 24(3):430-432.

Hoheisel, J., 1997, "Oligomer-chip technology" *Tibtech*, 15:465-469.

Kazimierczuk, et al, 1990, "Steroselective Synthesis of 2-Azapurine 2'-Deoxy-β-D-ribonucleosides by Nucleobase-Anion Glycosylation", *Liebigs Ann. Chem*, 1990:647-651.

Lin, et al., 1999, "Synthesis and Properties of a Novel phosphodiester analogue, nucleoside boraophosphorothioate", *Chem. Commun.* 1999:1517-1518.

Narang, et al., 1979, "Improved Phosphotriester Method for Synthesis of Gene Fragments", *Methods of Enzymology*, 68(6):90-98.

Bolli, Martin et al.: "Watson-Crick base-pairing properties of bicycle-DNA"; *Nucleic Acids Research*, 1996, vol. 24, No. 23, pp. 4660-4667.

Epplen, Cornelia et al.: "Differential stability of the $(GAA)_n$ tract in the Friedreich ataxia (STM7) gene"; Hum Genet, 1997, vol. 99, pp. 834-836.

Ginzinger, David G. et al., "Measurement of DNA Copy Number at Microsatellite Loci Using Quantitative PCR Analysis"; *Cancer Research,* 2000, vol. 60, pp. 5405-5409.

* cited by examiner

METHOD FOR THE DETERMINATION OF A NUCLEIC ACID USING A CONTROL

This application claims priority under 35 U.S.C. §119(a)–(c) to European Application No. 01 105 172.9, filed Mar. 2, 2001.

This invention is directed to a method for the determination of a target nucleic acid using a special control nucleic acid, a method for the amplification of a partial sequence of said target nucleic acid using primer(s) and a special control nucleic acid and a kit containing said control nucleic acid.

BACKGROUND OF THE INVENTION

The determination of nucleic acids has become an important tool in analytical chemistry, especially in health care. For example, infection diseases and genetic status can be easily determined on the basis of the presence or the amount of a nucleic acid indicative of said disease or status in samples received from the individual. For this reason methods were established using sequence specific hybridization of a nucleic acid, preferably an oligonucleotide, with a target nucleic acid indicative for that disease or genetic status. Sensitive techniques like the branched DNA-method (U.S. Pat. Nos. 5,681,702, 5,597,909, 5,545,730, 5,594,117, 5,591,584, 5,571,670, 5,580,731, 5,571,670, 5,591,584, 5,624,802, 5,635,352, 5,594,118, 5,359,100, 5,124,246 and 5,681,697), or methods detecting rRNA target nucleic acids (EP 0 272 009), which are present in high copy numbers in an organism, can be used for direct detection of a target nucleic acid in a sample from that organism. But many target nucleic acids are present in an organism in such low concentration, that a direct detection in a sample derived from that organism is not possible. Such targets need to be amplified before detection. Suitable amplification methods are for example LCR (U.S. Pat. Nos. 5,185,243, 5,679,524 and 5,573,907; EP 0 320 308 B1; WO 90/01069; WO 89/12696; and WO 89/09835), cycling probe technology (U.S. Pat. Nos. 5,011,769, 5,403,711, 5,660,988, and 4,876,187, and PCT published applications WO 95/05480, WO 95/1416, and WO 95/00667), Invader TM technology (U.S. Pat. Nos. 5,846,717; 5,614, 402; 5,719,028; 5,541,31 1; and 5,843,669), Q-Beta replicase technology (U.S. Pat. No. 4,786,600), NASBA (U.S. Pat. No. 5,409,818; EP-0 329 822), TMA (U.S. Pat. Nos. 5,399,491, 5,888,779, 5,705,365, 5,710,029), SDA (U.S. Pat. Nos. 5, 455,166 and 5,130,238) and PCR (U.S. Pat. No. 4,683,202).

In order to minimize false results in nucleic acid determinations, authorities in several countries require the use of control nucleic acids. Especially when using amplification methods such control nucleic acids are very important, because the amplification process can be strongly influenced by the reaction conditions, which could lead to misleading results. Sometimes inhibitory substances are contained in a sample, which could lead to false negative results.

In general one can distinguish external and internal controls. External controls, like classical positive and negative controls are normally used to check whether the assay runs properly or whether contaminants are contained. An internal control for example is useful for recognizing inhibitory substances possibly contained in a sample or can be used as a quantification standard in a quantitative assay. In contrast to an external control, which normally is tested in a separate reaction chamber, an internal control is preferably incubated in the same reaction chamber together with the analyte to be tested. Therefore, the control or the amplified product of that control has to be distinguishable from the analyte or from the amplified product of that analyte. When using an amplification method an internal control nucleic acid is being co-amplified essentially under the same reaction conditions as the target nucleic acid. These conditions include reagent concentrations, temperature, inhibitor concentration or enzymatic activities. Frequently used sequences for controls are derived from housekeeping genes (see Chelly et al. (1990) Eur. J. Biochem. 187:691–698; Mallet et al. (1995) J. Clin. Microbiol. 33:3201–3208), but also non-natural sequences are being used (Besnard et al. (1995) J. Clin. Microbiol. 32:1887–1893; Gilliland et al. (1990) Proc. Natl. Acad. Sci. USA 87:2725–2729; Wang et al. (1989) Proc. Natl. Acad. Sci. USA 9717–9721).

The amplified nucleic acid derived from the internal control can be distinguished from the amplified nucleic acid derived from the target nucleic acid for example by their different length or hybridization capability to a distinct probe (for reviews see: Clementi et al. (1990) PCR Methods Applic. 2:191–196; Clementi et al. (1995) Arch. Virol. 140:1523–1539). In all cases the nucleotide sequence of the internal control is partially or totally different from the target nucleic acid sequence. However the sequence and the length of a nucleic acid determine its GC-content, secondary structures and melting temperature and, therefore, is essential for its behavior in a hybridization and amplification reaction. A different sequence of an internal control in nearly all cases result in a different behavior of the control nucleic acid compared with that of the target nucleic acid. In contrast thereto an ideal internal control should mimic exactly the target nucleic acid in order to allow a proper monitoring of the reaction.

One of the most critical aspects in an amplification reaction is the binding of the primer to the target nucleic acid. Therefore internal controls are being used, which have the same primer binding sites as the target nucleic acid (see for example Gilliland et al. (1990) Proc. Natl. Acad. Sci. USA 87:2725–2729; Wang et al. (1989) Proc. Natl. Acad. Sci. USA 9717–9721; U.S. Pat. No. 5,219,727). This could lead to a competition in the reaction for the primers and could result in a decreased sensitivity of the assay.

Gilliland et al. (1990) Proc. Natl. Acad. Sci. USA 87:2725–2729 describe internal controls which nearly have the same nucleotide sequence as the target nucleic acid, but contain a new restriction enzyme cleavage site or the sequence of an intron region not contained in the target nucleic acid. Due to the very high homology of the internal control with the target, both nucleic acids as well as the amplificates can cross-hybridize with each other. Dependent on the detection method used, this can lead to wrong results especially in quantitative assays. Also, the described methods requires elaborous techniques like restriction enzyme digestion and agarose gel electrophoresis of the amplified products.

U.S. patent application No. US 2001/0006800 A1 describes related control nucleic acids which comprise the internal target sequence without the primer regions in an inverted orientation. This application does not describe controls which comprise the complementary target sequence in an inverted orientation nor controls comprising target primer sequences in an inverted orientation. Especially it is to note that inversion of the primer sequences would lead to sequences which do have different Tm's and GC-contents compared to the original primer sequences.

It is an object of the present invention to improve the methods for determination of nucleic acids, especially in avoiding all or a part of the disadvantages of the known methods.

SUMMARY OF THE INVENTION

The main aspect of the invention is to provide nucleic acids which mimic the properties of a target nucleic acid with regard to length, G/C content, secondary structure, and folding kinetic and further more, but which can be distinguished easily from the respective target nucleic acid by their sequence. To achieve this, a sequence is constructed, which covers essentially the region of said target nucleic acid to be determined or the complementary strand of said target nucleic acid region and which sequence is at least in part parallel-complementary to a strand of the target nucleic acid or to a strand complementary thereto. The parallel-complementary part or parts of the control nucleic acid sequence can extend from small stretches e.g. at least 8 nucleotides, preferred at least 10 nucleotides to the complete target nucleic acid region to be determined in the most extended case. In a preferred aspect of the present invention the parallel-complementary part or parts contain probe binding site sequence(s).

In another preferred aspect, particularly, if the target nucleic acid region to be determined is amplified for determination, the control nucleic acid according to the present invention could also contain primer binding site(s) being parallel complementary to the respective primer binding site(s) of the target nucleic acid region.

Such control nucleic acids can be used for example as internal controls in hybridization and amplification methods and are therefore useful in the chemical analytic and medical diagnostic field.

The invention is also related to a method for the amplification of a target nucleic acid region in a sample comprising the step:

amplifying said target nucleic acid region and a known amount of control nucleic acid, said control nucleic acid covering essentially said target nucleic acid region to be amplified or the complement of said target nucleic acid region, whereby the region of said control nucleic acid covering essentially the region of said target nucleic acid to be amplified or the complement of said target nucleic acid contains at least one contiguous sequence of at least 8 nucleotides being essentially parallel-complementary to said target nucleic acid or to the complementary strand of said target nucleic acid.

With regard to amplification methods such control nucleic acids bear additional advantages. If a primer-binding site of these nucleic acids is parallel-complementary to the primer binding site of the target, these controls mimic the properties of the primer binding to the target, although the sequences of primer binding sites and primers of the control nucleic acid are different from that of the target nucleic acid. A competition of the primers for amplification of the target and the control is avoided and the sensitivity and linear range of the assay can be improved.

A control as mentioned can be used in any hybridization and amplification method for determination of nucleic acids. The use of this control nucleic acid is triggered by the need for a control that reflects the characteristics of the target nucleic acid to be determined, but which can be still separately detectable.

DETAILED DESCRIPTION OF THE INVENTION

Figure 1:
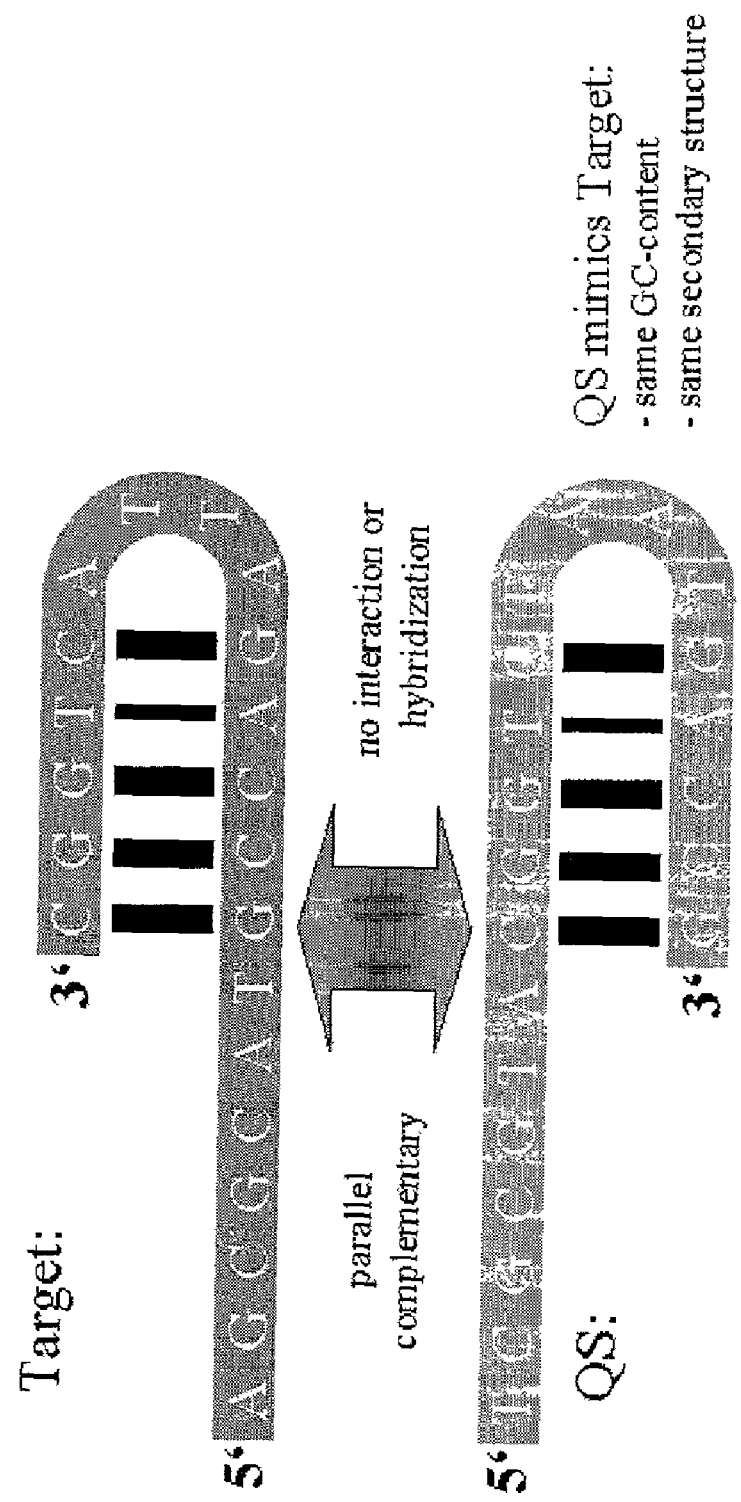
FIG. 1 shows an example of a nucleotide acid sequence and its parallel-complementary sequence as well as their capabilities to form similar secondary structures. (QS: control nucleic acid to be used in a quantitative or qualitative assay)

The invention is mainly based on the observation that a first nucleic acid having a sequence being parallel complementary to another second nucleic acid sequence has very similar hybridization properties defined by its length, GC-content, Tm and secondary structures compared to the first nucleic acid sequence, although the sequence is completely different. Such a nucleic acid can be used as control nucleic acid for determination of a target nucleic acid, because the control nucleic acid and the target nucleic acids and its amplificates have a very similar hybridization behavior, but are still separately detectable by their different sequences.

A preferred control nucleic acid according to the present invention covers essentially the region of the target nucleic acid to be determined characterized in that the region of said control nucleic acid covering essentially the region of said target nucleic acid to be determined or the complement of said target nucleic acid contains at least one contiguous sequence of at least 8 nucleotides being essentially parallel-complementary to said target nucleic acid or to the complementary strand of said target nucleic acid.

Covering essentially the region of the target nucleic acid to be determined in this context means, that this region of the control nucleic acid consists of one or more parts, whereby the sequence of each part is essentially identical or essentially parallel-complementary to the according part of the target nucleic acid region to be determined or to the complementary strand. Therefore, this region of the control nucleic acid is either essentially identical, essentially parallel-complementary or in part essentially parallel-complementary, whereas the other part is essentially identical to the relevant region of the target nucleic acid region to be determined or to the complementary strand of the target nucleic acid. Therefore this control nucleic acid region has essentially identical hybridization properties compared with the region of the target nucleic acid region to be determined or the complementary strand of the target nucleic acid. Slight changes in secondary structure behavior can occur if too many essentially parallel-complementary and essentially identical parts are combined in the control nucleic acid, whereas this does not effect the GC-content. In order to guarantee that the behavior of the control still mimics the behavior of the target, it is preferred that the control nucleic acid region covering the region of the target nucleic acid to be determined consists of fewer than 10, more preferred fewer than 6 parts being either essentially parallel-complementary or essentially identical.

Since essentially identical or identical sequences cannot easily be distinguished, it is very important that the region of the control nucleic acid covering the region of the target nucleic acid to be determined contain at least one contiguous sequence of at least 8 nucleotides, more preferred at least one sequence of at least 10 nucleotides being essentially parallel-complementary to said target nucleic acid sequence in order to allow a distinct determination of target nucleic acid and control nucleic acids or their amplificates for example by probe hybridization.

A part of a first nucleic acid is parallel complementary to a second nucleic acid or a part of it, if the sequence of that first nucleic acid is identical with the sequence of the complementary strand of the second nucleic acid sequence or a part thereof when the sequence of the complementary strand of the target nucleic acid sequence is read in reverse orientation. For natural nucleic acids this means reading the sequence from the 3'-end to the 5'-end. An example is given in FIG. 1. The parallel complementary sequence of the nucleic acid sequence

```
5'-AGCGCATGCCAGATTACTGGC-3'  (Seq. ID No.1)
is

5'-TCGCGTACGGTCTAATGACCG-3'  (Seq. ID No.2).
```

The parallel complementary sequence to the complement strand is
5'-CGGTCATTAGACCGTACGCGA-3' (Seq. ID No. 17).

The parts of the control nucleic acids according to the present invention need not to be 100% identical or 100% parallel-complementary to the target nucleic acid, although this case is preferred. It is sufficient, if these parts are either essentially identical or essentially parallel-complementary. Essentially identical means that the homology of this part or these parts of the control nucleic acid are more than 80%, more preferred more than 90% compared with the relevant parts of the target nucleic acid. Essentially parallel-complementary means that the homology of this part or these parts of the control nucleic acid are more than 80%, more preferred more than 90% parallel-complementary compared with the relevant parts of the target nucleic acid.

For exact determination of homology and complementarity it is preferred to use suitable computer programs like FastA (Pearson and Lipman, *Proc. Natl. Acad. Sci. USA* 85: 2444–2448 (1988); WISCONSIN PACKAGE™ sequence analysis software version of FastA, default settings: wordsize 2(p-p), 6(n-n); Don't show scores whose E( ) value exceeds 10.0(p-p), 2.0(n-n)).

Control nucleic acids according to the present invention are also useful in hybridization and amplification reactions for determination of target nucleic acids with related sequences like allelic forms. For this purpose it is not necessary to synthesize a new control for each allelic form of a target nucleic acid.

A control nucleic acid according to the present invention to be used in a hybridization method as a pure control to monitor for example one probe hybridization step covers essentially the region of the target nucleic acid to be determined characterized in that the region of said control nucleic acid covering essentially the region of said target nucleic acid to be determined or the complement of said target nucleic acid contains at least one contiguous sequence of at least 8 nucleotides being essentially parallel-complementary to said target nucleic acid or to the complementary strand of said target nucleic acid. The most important region in such methods is the region of the target nucleic acid actually bound by the target-specific probe, which is actually the region of the target nucleic acid being determined. Therefore, in most cases it is sufficient that this region is being covered by the internal control. In case this region is shorter than 15 nucleotides, more preferred shorter than 10 nucleotides it is preferred that the relevant region of the control nucleic acid is essentially parallel-complementary to the probe hybridization region of the target nucleic acid. If the probe hybridization region of the target nucleic acid is longer than 15 nucleotides, more preferred longer than 10 nucleotides, the relevant region of the control nucleic acid may be either fully parallel-complementary to the probe hybridization region of the target nucleic or the region be in part essentially parallel-complementary, whereas the other part(s) is essentially identical. Using an essentially complementary, preferred a complementary probe for hybridization with such a control nucleic acid it is possible to mimic the hybridization of the target nucleic acid with its probe, but still allow a separate determination of both hybridization complexes.

An amplification control allows to monitor an amplification process. When looking for example at a typical PCR-assay this can include primer-hybridization steps, elongation of the primers, amplification efficiency or/and also further probe-hybridization steps. A preferred amplification control according to the present invention can contain regions flanking the region covering essentially the region of the target nucleic acid being amplified, because the preferred primers used for amplification of the control are either essentially parallel-complementary or essentially identical, more preferred parallel-complementary or identical to the primers for amplification of the target dependent on the sequence of the control. Therefore the amplificate of the control nucleic acid does not contain the flanking regions of the control but only the region which essentially covers the region of the target nucleic acid being amplified and the length of both amplificates are essentially identical.

The region of the control nucleic acid which essentially covers the region of the target nucleic acid to be amplified can be built of several parts which are either essentially parallel complementary or essentially identical to the according part of the target nucleic acid as described above. Preferred combinations of the control nucleic acid covering the region of the target nucleic acid to be amplified are listed in table 1:

TABLE 1

| Primer-site(s) | Probe-site(s) (if present) | Non-probe/non-primer region |
|---|---|---|
| Id | Pc | Id |
| Id | Pc | Pc |
| Pc | Pc | Pc |
| Pc | Pc | Id |

TABLE 1-continued

| Primer-site(s) | Probe-site(s) (if present) | Non-probe/non-primer region |
|---|---|---|
| Pc | Id | Pc |
| Pc | Id | Id |

Id = essentially identical,
Pc = essentially parallel-complementary to target

According to the invention only the sequence of the bases is important, whereas the backbone need not to necessarily be the natural sugar-phosphate backbone. Therefore it is also possible to use nucleic acids as controls according to the present invention having a modified backbone or a non natural backbone like Peptide Nucleic Acid (WO 92/20702). When using control nucleic acids containing base analogues it should be taken care that theses base(s) have similar properties to the complementary natural base contained in the relevant position of the target nucleic acid sequence in order to mimic the hybridization behavior of the target nucleic acid as closely as possible. Also it should be taken care that when using a control nucleic acid as an amplification control nucleic acid, the nature of the control nucleic acid should allow the amplification of the control nucleic acid with the amplification method used.

A control nucleic acid according to the present invention can be constructed on the basis of the sequence of the coding strand of RNA or DNA, or the strand complementary thereto. The controls can be for example chemically synthesized and cloned in suitable vectors like plasmids, phage nucleic acids, or in the genome of bacteria or viruses or be used as they are constructed. Such control nucleic acids can be amplified in vitro or be produced in bacteria transfected with the vectors containing the nucleic acid sequence of the controls. Such control nucleic acids can be used directly in the test or be packaged, for example as armored RNA (U.S. Pat. No. 5,677,124) or be packaged in liposomes.

The target nucleic acid is the nucleic acid to be determined. This can be of any origin, for example of viroid, viral, bacterial, or cellular origin. It can be derived from solutions, like blood, serum, plasma or urine, from suspensions, fixed on solids, cell containing media, cell smears, fixed cells, tissue sections or fixed organisms. Preferably the nucleic acid to be determined is in solution. The nucleic acid to be determined can further be a nucleic acid derived from the target nucleic acids, for example by recombination, fragmentation, amplification and/or cDNA formation from RNA.

The target nucleic acid is usually brought into available form by processing the original sample with one of various methods. This comprises for example change of pH (alkaline), heating, cyclic changes of temperature (freezing/thawing), change of the physiological growing conditions, use of detergents, chaotropic salts or enzymes (for example proteases or lipases), alone or in combination. If the control nucleic acid according to the present invention is added to a sample prior or during the sample preparation step, these control nucleic acids can also be used as controls for the sample preparation in addition to the subsequent amplification and/or hybridization step. For this purpose the control nucleic acid can be added to the sample as DNA or RNA depending on the nature of the target nucleic acid. It can also be packaged similarly like the target nucleic acid, which is often contained in the sample attached to proteins or other cellular or viral components. In order to mimic the target nucleic acid more closely, the control nucleic acid may be packaged for example in a protein coat, as for example in armored RNA.

The control nucleic acids according to the present invention can be used for example as controls, preferably as internal controls in hybridization methods like the branchedDNA method or the determination of ribosomal RNA targets or may be also useful for array hybridization methods.

They are also useful for example as controls, preferably as internal controls, in target amplification methods, like TMA, SDA, NASBA, LCR, and PCR. The preferred method is PCR. In principle, a target nucleic acid for example indicative for an infectious agent or a genetic status is used as a template to which a primer can sequence specifically bind under suitable reaction conditions. Dependent on the method used the primer can be for example extended with nucleotide monomers using a polymerase or ligated with a further primer hybridized nearby. In case such an amplification product itself can directly or indirectly serve as a template one can amplify the target nucleic acid exponentially. Also known are linear amplification methods. The amplification products can be detected directly, for example by agarose gel electrophoresis or by performing a further hybridization reaction with at least one sequence specific probe.

A primer according to the present invention is a molecule capable of being extended or modified preferably by enzymes, more preferably by a polymerase of for instance procaryotic origin, when hybridized to a nucleic acid template. When using PCR thermostable polymerases, like *T. aquaticus* DNA-polymerase, are preferred. The extension adds mononucleotide units from monodesoxyribonucleosidetriphosphates to one end of said primer, preferably the 3'-OH-terminal end. The overall length and base sequence of a primer is dictated by the required specificity of the amplification reaction. Preferred primer lengths for performing PCR are from 10 to 40, most preferred from 15 to 30 base containing subunits, selected from mononucleotides and/or nucleic acid analog monomers. In general primers of that length are also useful for other amplification methods. If more than one primer is used for amplification, for example when using PCR or amplifying multiple target nucleic acids in one reaction, preferably primers are used which cannot hybridize to each other, because they do not contain any stretch of more than 5 consecutive complementary bases.

For PCR the locations of hybridization of the primers are typically chosen such that there is a stretch of at least 10, but not much more than 1000, preferably from 100 to 500 nucleotides between their original 3'-ends, in the hybrid of the extension products.

Generally, it is important that a primer binds sufficiently strong to the target nucleic acid in order to allow amplification under the reaction conditions, but care must be taken that the primer preferably only binds to the target nucleic acid and binding to other nucleic acids which may be contained in a sample should be avoided. Therefore primers are preferred which are 10 to 40 nucleotides long, more preferred 15 to 30 nucleotides long. Preferably the primers are oligonucleotides.

A probe is a molecule used for the determination of a target nucleic acid or an amplified target nucleic acid. It can also be used to determine the sequence of a target nucleic acid or amplified target nucleic acid. For this purpose probes can be used which have different sequences. Such probes can also be used for example for the determination of different allelic forms of a target nucleic acid or for a genus and species-specific determination of a target. Probes are preferably oligonucleotides, but also analogues, for example PNA, can be used. In order to allow a sequence specific hybridization the probes are preferably longer than 10 nucleotides, even more preferred have a length of 10 to 40 nucleotides. In order to allow a detection of the target nucleic acid, the amplificates and the according probe-hybrization complexes, the probes or/and the primers used can be coupled to groups which can be detected directly or indirectly or which allow an immobilization of the target nucleic acid, the amplificates and the according probe-hybrization complexes to a solid phase.

A label is generally known to a man skilled in the art as being a group which is detectable or can be made detectable for determining the presence of an analyte. Well-known labels are fluorescent labels, like fluoresceine, electrochemiluminescent labels, like ruthenium complexes, or moieties that can be recognized by another molecular entity, like haptens which can be recognized by an antibody raised against this hapten or moieties that can be immobilized, like biotin (to streptavidin coated solid phases, like tubes or beads). Labels can be for example bound to the probe(s) or primer(s), or can be incorporated into the amplified nucleic acids as labeled nucleoside-tri-phosphate units. Also labels can be used which allows the detection of the target nucleic acid or amplified target nucleic acid by other means for example by intercalation of that label or a labeled intercalator into double stranded DNA. Labels can either be used for detection of the primers or probes or any product having incorporated said primer, to determine the hybrid formed by said primer or probe with a nucleic acid to be determined or an amplified target nucleic acid incorporated labeled nucleotides.

A solid phase is a solid not substantially soluble in the reaction mixture, for example in the form of a bead, a net, the inner surface of a tube, a microtiter plate or a chamber of a device. It is essentially used to contain the reaction mixture, but in case of intention to bind an immobilisable probe, primer or control nucleic acid to it, it may contain on its surface reagents or a coating being capable to recognize and bind a moiety of said probe, primer or control nucleic acid.

Using heterogeneous detection methods, the determination, for example by probe hybridization, is performed after the amplification step. The hybridization complex can be detected in solution or after immobilization on a solid phase. Also known are homogenous detection formats, which allows to determine the amplified nucleic acid in the reaction mixture without further separating or washing steps. For this purpose several probe hybridization formats are known, like Taqman (U.S. Pat. Nos. 5,210,015 and 5,487,972), Fluorescence Resonance Energy Transfer (U.S. Pat. No. 4,996,143), Molecular Beacon (WO-95/13399, U.S. Pat. Nos. 5,119,801 and 5,312,728), Sunrise (U.S. Pat. No. 5,866,336), Scorpions (PCT/GB98/03521). Such methods can be used to detect the level of synthesized amplificate over the whole amplification reaction. When using an internal control, for example an internal control according to the present invention, in a reaction or for determination of multiple targets the signals measured for each target and control can be distinguished from each other. For that reason one can use for example different labels attached to the different probes or primers, which allows a simultaneous measurement of the different targets and controls or the amplified nucleic acids derived from these nucleic acids in the reaction mixture.

The control nucleic acid according to the present invention is a nucleic acids, that may be chemically synthesized, may be cloned, amplified or isolated by other means known in the art. It is preferably made of RNA- or DNA-monomers, but can also contain natural or non-natural base or sugar analogues. Due to the parallel complementary part(s) the control nucleic acids have a different sequence compared with the sequence of the target nucleic acid and in most cases such sequences have to be produced synthetically at least once by known methods, like the phosphoramidite technology. In order to allow the production of longer nucleic acids according to the present invention one can synthesize short, about 40 to 120 bases long oligonucleotides which overlap both strands of the desired control nucleic acid in a staggered mode. After hybridization of these oligonucleotides and a following ligation step the nucleic acid can for example be cloned into a vector or can be used directly as described herein. The cloned nucleic acid can be amplified for example in bacteria and isolated using standard methods (Sambrook et al., Molecular Cloning: A laboratory Manual, Cold Spring Harbour Laborator, 2001, ISBN 0879695765 ). If the nucleic acid is an RNA it can be synthesized for example by in vitro transcription using a vector, which contains a suitable promoter sequence, like the T7 phage promoter sequence. The nucleic acids may be used as naked nucleic acid or be packaged in particles, for example as armored RNA (U.S. Pat. No. 5,677,124), or be embedded in viroid, viral, bacterial, or cellular organisms.

Such nucleic acids are for example useful for controlling nucleic acid hybridization and amplification reactions. They can be used to identify false negative results due to inhibitors present in a sample or as standards in a quantitative assay. The control can be processed in a parallel reaction in different vessels (external control) or co-processed in the same reaction vessel (internal control) as the target, whereas the latter case is preferred.

The essentially parallel complementary part(s) in the control construct can include one or more probe binding site or/and one or more primer binding site or/and one or more primer/probe flanking regions, in the most extended case the whole sequence of the corresponding target nucleic acid.

This means that during processing of a control nucleic acid according to the present invention primers or/and probes can be used, that are essentially parallel-complementary, preferred parallel-complementary to those used for processing of the target nucleic acid. Corresponding primers and probes exhibit same GC content and hybridizing properties, that mainly reflect probe- and primer-hybridization efficiencies and amplification efficiencies, but no competition with regard to these reaction components occurs, because the primers or/and probes binding to the control nucleic acid cannot bind to the target nucleic acid and vice versa.

In case of only low amounts of target nucleic acid in a sample such a competition could eventually lead to an absence of amplification of the target or reduced probe-binding. Therefore, the use of parallel-complementary primers and probes can increases sensitivity and linear range of an assay. Although it should be noted, that using identical primers for amplification of the target nucleic acid and the control nucleic acid bears the advantage that one set of primers is sufficient and a direct control of the target-specific primers is possible.

In a qualitative test, the control nucleic acid of the present invention can be used to identify false negative results, preferentially used as an internal control nucleic acid. Due to its ability to mimic the target very close, it's subjected to inhibitors in the same manner. Especially, when the control nucleic acid is added to the reaction in low concentration, because in this case the system reacts very sensitive to the occurrence of inhibitory substances. Such control nucleic acids can also be used as standards, preferably as an internal standard, for example as a mean for standardizing of results of parallel experiments.

In a quantitative test, the control nucleic acid of the present invention can be used as a quantitative standard to determine starting level of a target nucleic acid contained in a sample. A known amount of the standard nucleic acid is being co-amplified essentially under the same reaction conditions together with a target-nucleic acid, preferred as an internal quantitative standard. After amplification or, in case of a homogeneous detection, during the amplification reaction, the amount of amplified target nucleic acid and the amount of amplified standard nucleic acid is determined. Using those and knowing the initial amount of standard nucleic acid in the reaction it is possible to calculate the initial amount of target nucleic acid, which was present in the sample prior to amplification. Several methods for quantification are known in the art, including for example concepts using internal standard curve, external standard curve and Payan-Model (see for example Haberhausen et al., Journal of Clinical Microbiology, Vol 36, p. 628 to 633). It should be noted that it is not necessary to measure absolut amounts of amplificates synthesized. For most purposes relative amounts are sufficient, which can be determined for example by hybridization of the amplificates with labeled probes and measuring the signal intensity of the hybridization complexes.

In a preferred embodiment, the control nucleic acids of the present invention are used in the polymerase chain reaction (PCR), described in U.S. Pat. Nos. 4,683,195; 4,683,202 and 4,965,188, Saiki et al., Science 230:1350–1354; mullis et al., 1986, Cold Spring Harbor Symp. Quant. Biol. 51:263–273; and Mullis and Faloona, 1987, Methods Enzymol. 155:335–350. However the invention is not restricted to any hybridization or amplification method.

The control nucleic acid can be added at certain stages of the reaction. Usually nucleic acids of a sample, for example blood, serum, sputum or tissue sample are at least partially purified by a sample preparation method known in the art. The particular method used is not a critical part of the present invention. The control nucleic acid can be added prior to sample preparation allowing the control nucleic acid to be co-processes with the target nucleic acid contained in the sample. This allows to monitor the sample preparation step in addition to the following amplification or/and probe hybridization step.

In the alternative the control nucleic acid can also be added to the amplification reaction mixture after sample preparation in order to allow monitoring of the a co-amplification of the target nucleic acid and the control nucleic acid, but can also be added after amplification, at the probe-hybridization step, to monitor the hybridization step.

Preferably for amplification of the control nucleic acid primer(s) are used which are either essentially identical or essentially parallel-complementary to the primers used for amplification of the target nucleic acid. As such control specific primers have essentially the same melting temperature as the respective target-specific primers, it is easier to find an appropriate temperature cycle profile suitable for amplification of the target nucleic acid and the control nucleic acid compared with other multiplex amplification reactions. The same applies if probes are used for the determination of control nucleic acids or amplified control nucleic acids, the probes being essentially parallel-complementary compared with the probes used for determination of the target nucleic acid or amplified target nucleic acids.

When amplifying target nucleic acids and control nucleic acids using PCR, the reaction mixture typically in addition to target nucleic acid contains the control nucleic acid, specific primers and optionally probes for homogenous detection and further reaction components like appropriate buffers (for example Tricine), divalent cations like $Mg^{2+}$ or $Mn^{2+}$, a polymerase, preferably a thermostable polymerase, and the four desoxyribonucleotides (dATP, dCTP, dGTP and dTTP). The amplification reaction can be performed with a thermocycler known in the art, for example an PE 9600 (or ABI Prism 7700) (Perkin Elmer Corp.) using a temperature cycle profile allowing denaturing double stranded nucleic acid, sequence-specific hybridization of the primers to the target and control and elongation of the primers by the polymerase. This temperature cycle can be repeated as often as necessary to allow synthesizing sufficient amounts of amplified nucleic acids for determination. Usually 30 to 40 cycles are performed.

In case the amplified nucleic acids are determined by probe hybridization following amplification, the amplified nucleic acids are denatured for example by heat or alkali, neutralized (if necessary), the probe(s) are added and hybridization of the probe to the amplified nucleic acids is performed under suitable conditions (temperature and chemical milieu). Such conditions can be determined easily by an expert making a few comparative experiments. The specific hybridization complexes can be detected using labels and other detection means as described herein.

In case of a homogenous determination format, the amplified nucleic acids are detected in the amplification reaction mixture preferably during the amplification reaction. If the amplified nucleic acids are determined using specific probes, the probes are added to the amplification reaction prior to starting the amplification reaction. In addition such a determination format bears the advantage, that usually the tube need not to be opened after amplification and contamination risks are minimized. The hybridization of probes to the amplified nucleic acids during the amplification reaction can be monitored using different methods. Very often the probes are labeled with fluorescent labels, which can be detected during the reaction if suitable detectors are integrated into the thermocycler (i.e. an ABI Prism 7700, Perkin Elmer). In order to allow the detection only of probes, which have been hybridized or hybridize to the specific amplified nucleic acid, several formats have been established, which are referenced herein. Using the TaqMan-format the hybridized probe is partially digested by the polymerase cutting a first quenching label from the 5'-end of the probe, which allows to measure the signal emitted by a second, preferably fluorescent label attached to the probe. This fluorescence signal is used as a measure for the amount of specific amplified nucleic acid synthesized in the reaction. As the probe specific to the control nucleic acid preferably has another fluorescent label than the probe specific to the target nucleic acid emitting light having another wavelength, the signals of both probes can be measured separately within the same reaction tube. The two signals can be used to calculate, for example, the initial amount of target nucleic acid present in the sample.

A preferred subject of the present invention is a method for quantitation of a target nucleic acid comprising the steps
a) amplifying a region of said target nucleic acid and a known amount of control nucleic acid, said control nucleic acid covering essentially said target nucleic acid region to be amplified or the complement of said target nucleic acid region, whereby the region of said control nucleic acid covering essentially said target nucleic acid region to be amplified or the complement of said target nucleic acid contains at least one contiguous sequence of at least 8 nucleotides being essentially parallel complementary to said target nucleic acid or to the complementary strand of said target nucleic acid, b) detecting a signal indicative for the amount of amplification product obtained from said control nucleic acid and detecting a signal indicative for the amount of amplification product obtained from said target nucleic acid c) calculating the amount of said target nucleic acid using the known amount of said control nucleic acid, the signal indicative for the amount of amplification product obtained from said control nucleic acid determined in step b) and the signal indicative for the amount of amplification product obtained from said target nucleic acid determined in step b).

A further subject of the present invention is a control nucleic acid in a reaction for the amplification of a target nucleic acid region, said control nucleic acid covering essentially the region of said target nucleic acid to be amplified or the complement of said target nucleic acid region, whereby the region of said control nucleic acid covering essentially the region of said target nucleic acid to be amplified or the complement of said target nucleic acid contains at least one contiguous sequence of at least 8 nucleotides being essentially parallel complementary to said target nucleic acid or to the complementary strand of said target nucleic acid.

A further subject of the present invention is a composition of matter comprising a target nucleic acid and a control nucleic acid, which composition is present in a hybridization or amplification reaction mixture for detecting the target nucleic acid region and whereby said control nucleic acid covers essentially the region of said target nucleic acid to be determined or the complement of said target nucleic acid region characterized in that the region of said control nucleic acid covering essentially the region of said target nucleic acid to be determined or the complement of said target nucleic acid contains at least one contiguous sequence of at least 8 nucleotides being essentially parallel complementary to said target nucleic acid or to the complementary strand of said target nucleic acid.

A further subject of the present invention is a kit for amplification of a target nucleic acid comprising of an instruction manual and at least one container containing at least a control nucleic acid, whereby said control nucleic acid covers essentially the region of said target nucleic acid to be amplified or the complement of said target nucleic acid region characterized in that the region of said control nucleic acid covering essentially the region of said target nucleic acid to be amplified or the complement of said target nucleic acid contains at least one contiguous sequence of at least 8 nucleotides being essentially parallel complementary to said target nucleic acid or to the complementary strand of said target nucleic acid. Further preferred kits contain in addition to the manual and the control nucleic acid other reaction components like target or control specific probes, target or control specific primers, reaction buffers, nucleoside-triphosphates or enzymes like a polymerase. These components can be packaged into the first container of such a kit, but can also be contained in one or more further containers. Also preferred is a kit useful for detection of a target nucleic acid using hybridization methods which contains an instruction manual and at least one control nucleic acid according to the present invention.

A further subject of the present invention is the use of a control nucleic acid as a control in a reaction for amplification of a target nucleic acid region or in a hybridization reaction for determination of a target nucleic acid region, whereby said control nucleic acid covers essentially the region of said target nucleic acid to be amplified or hybridized or the complement of said target nucleic acid region characterized in that the region of said control nucleic acid covering essentially the region of said target nucleic acid to be amplified or hybridized or the complement of said target nucleic acid contains at least one contiguous sequence of at least 8 nucleotides being essentially parallel complementary to said target nucleic acid or to the complementary strand of said target nucleic acid.

The present invention is exemplified by the following examples:

EXAMPLES

Example 1

Design of a Probe Sequence, that is Parallel Complementary to the HCV Target Probe Sequence For detection of HCV nucleic acid in a Taqman assay the following probe, binding to the HCV-amplicon (Seq. ID No. 10) can be used:

```
ST650 (Seq. ID No 3):
5' (Cy5-) CGG TGT ACT CAC CG(FAMs) TTC CGC AGA CCA CTA TGG C-PO4-3'
```

Cy5: Oligonucleotid-derivatisation with Pentamethin-di-indocarbocyanin using Alkylphosphatidyl-Linker (Pharmacia Biotech Cy5-N-ethyl-Phosphoramidit)Fams: Oligonucleotid-derivatisation with 6-Carboxy-fluorescein using 2-(Amino-cyclohexyl-) propan-1,3-diol-Linker (Biogenex CX-FAM-Phosphoramidit)

All HCV specific sequences enclosed in this application are derived from the sequence of the HCV type I genome (NCBI, Genbank Accession No. AF054249 or AJ000009).

At best the probe for internal control detection mimics the target probe exactly, but is distinguishable of the target probe. The parallel complementary sequence of the target probe, called ST650pc (Seq. ID No. 5), can be used as such an internal control probe. ST650pc has the same GC-content, GC/AT sequence, length, secondary structure and therefor the same melting temperature as the target probe. Furthermore, since G and A are substituted by C and T, respectively, and vice versa, it is distinguishable to the target probe. ST2535 (Seq. ID No. 4) contains a sequence which is not related to the sequence of HCV, e.g. is not essentially identical or essentially parallel-complementary to the sequence of HCV. An internal control containing a binding sequence for ST2535 can be used together with the probe ST2535 to control the target nucleic acid determination reaction. Probes and controls containing a sequence unrelated to that of the target nucleic acid sequence are often used in the prior art. In contrast thereto ST650pc (Seq. ID No. 5) has the potential to mimic target probe perfectly.

ST650pc (Seq. ID No. 5) probe can be used with all internal control or quantification standard constructs containing a ST650pc binding sequence.

```
ST2535 (Seq. ID No.4):
5' (Cy5-) TGG ACT CAG TCC T(HEXs)T GGT CAT CTC ACC TTC T-PO4 3'
```

HEXs: Oligonucleotid-Derivatisation with Hexachloro-6-carboxy-fluorescein using 2-(Amino-cyclohexyl) propan-1, 3-diol-Linker (Biogenex CX-HEX-Phosphoramidit)

```
ST650pc (Seq. ID No.5):
5' (CY5-) GCC ACA TGA GTG GC(HEXs) AAG GCG TCT GGT GAT ACC G-PO4 3'
```

Figure 2:
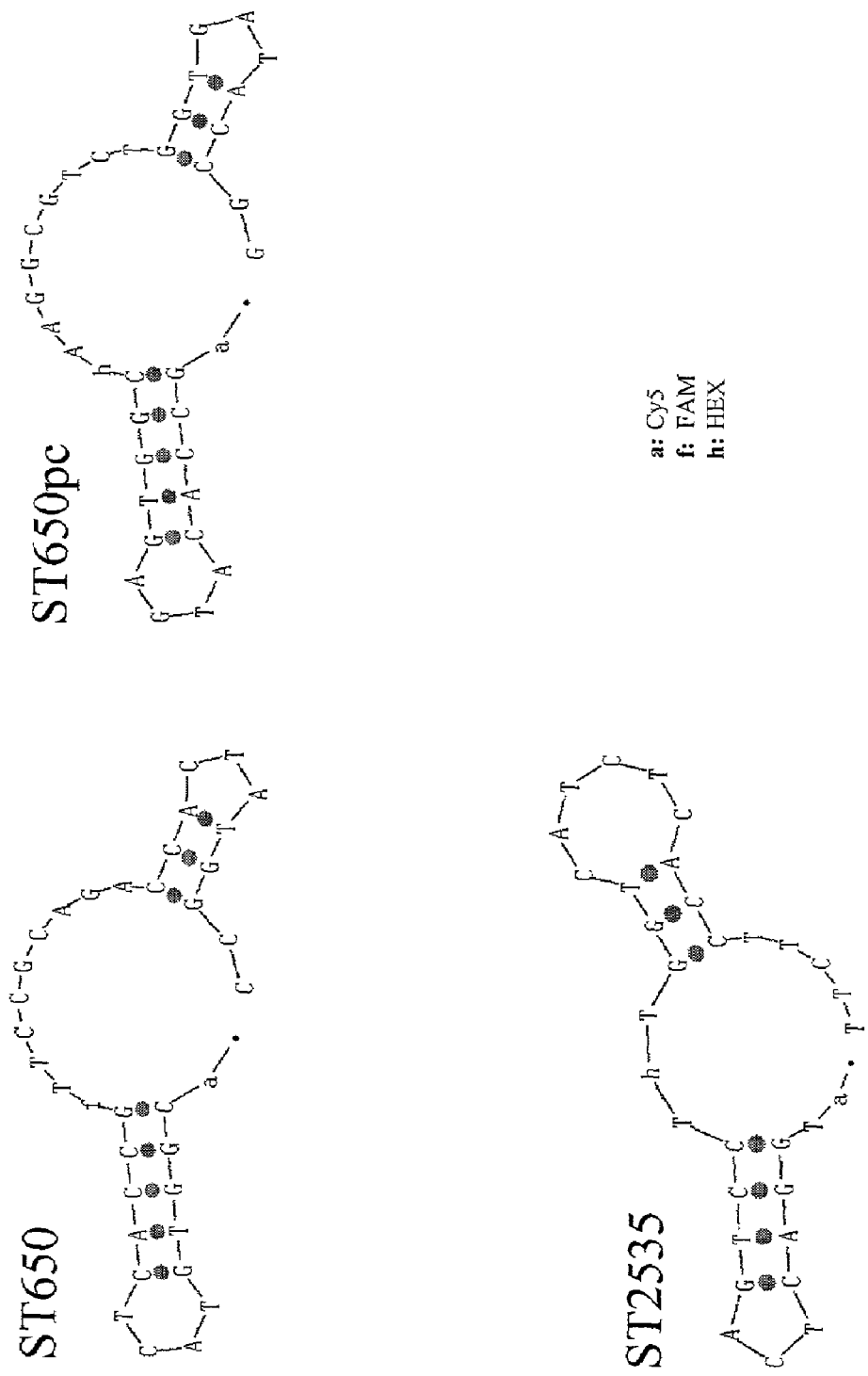
FIG. 2 shows the prediction of secondary structures done with Mfold version 3.0 (copyright 1996 Dr. M. Zuker, M. Zuker, D. H. Mathews & D. H. Turner, Algorithms and Thermodynamics for RNA Secondary Structure Prediction: A Practical Guide, In RNA Biochemistry and Biotechnology, J. Barciszewski & B. F. C. Clark, eds., NATO ASI Series, Kluwer Academic Publishers, (1999)) for the probes ST650 (HCV-specific probe), ST650pc (parallel complementary to ST650) and ST2535 (unrelated sequence).

Prediction of secondary structures was done using the software Mfold version 3.0 (copyright 1996 Dr. M. Zuker, M. Zuker, D. H. Mathews & D. H. Turner, Algorithms and Thermodynamics for RNA Secondary Structure Prediction: A Practical Guide, In RNA Biochemistry and Biotechnology, J. Barciszewski & B. F. C. Clark, eds., NATO ASI Series, Kluwer Academic Publishers, (1999)). As can be seen in FIG. 2 the predicted secondary structures are identical between target probe and parallel complementary probe.

Example 2

Design of Primer Sequences, that are Parallel Complementary to the HCV Target Primer Sequences and Comparison of Likely Formed Secondary Structures Formed by Target Primers and Parallel Complementary Primers:

For amplification of HCV nucleic acid the following primers are used:

```
ST280 (Seq ID No 6):
5' GCA GAA AGC GTC TAG CCA TGG CGT TA 3'

ST778 (Seq ID No 7):
5' GCA AGC ACC CTA TCA GGC AGT ACC ACA A 3'
```

The parallel-complementary sequences of these amplification primers are

```
ST280 pc (Seq ID No 8):
5' CGT CTT TCG CAG ATC GGT ACC TCA AT 3'

ST778 pc (Seq ID No 9):
5' CGT TCG TGG GAT AGT CCG TCA TGG TGT T 3'
```

These designed internal primers are used for amplification of the internal control. Amplification of the internal control is non-competitive, since target and internal control use different primers for amplification. Nevertheless, the designed parallel complementary primers are structural very close to target primers, with regard to GC content, GC/AT sequence, length, secondary structure and therefor melting temperature. ST280pc and ST778pc can be used as amplification primers for all internal control and quantification standard constructs that are non competitive and contain appropriate primer binding sites.

Figure 3:
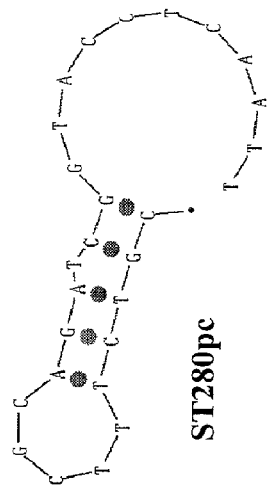
FIG. 3 shows the prediction of secondary structures done with Mfold version 3.0 for the primers ST280 (HCV-specific), ST280pc (parallel complementary to ST280), ST778 (HCV-specific) and ST778pc (parallel complementary to ST778).
Figure 3:
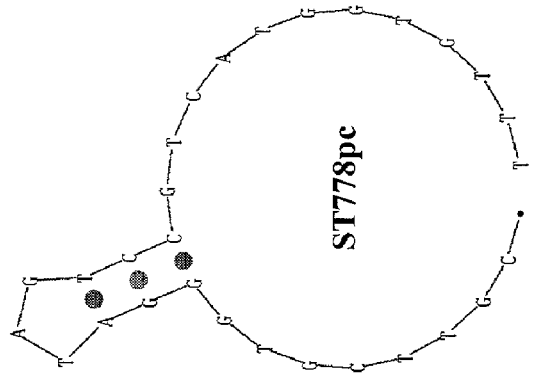
Figure 3:
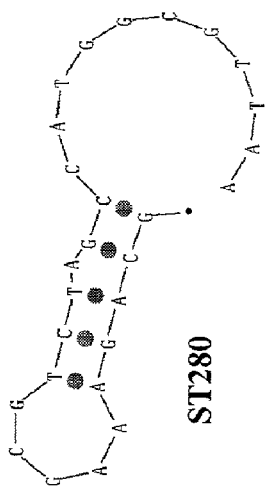
Figure 3:
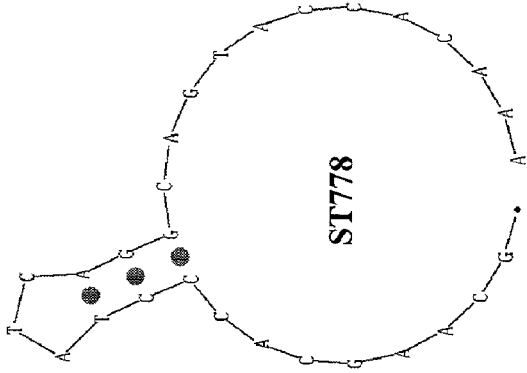

Predictions of secondary structures, done with Mfold version 3.0, are identical between target primers and parallel-complementary primers (see FIG. 3).

Example 3

Construction of an Internal Control for Non-Competitive Qualitative and Quantitative Nucleic Testing of HCV, that is Parallel Complementary to HCV Sequence:

A double stranded DNA fragment was cloned, using overlapping oligonucleotides with a length of 60–120 b, that is parallel complementary to a 5'-fragment of HCV type I genome including the highly conserved 5'-UTR region. The synthesized and cloned fragment is 943 bp long and cloned into the BglII/HindIII site of an aRNA expression vector (AMBION, Austin, USA). Expression results in an armored RNA particle that contains RNA including the gene for MS-2 coat protein, MS-2 packaging signal and the parallel complementary sequence of 5' HCV fragment. This RNA is distinguishable from the target, but due to parallel complementarity, GC-content and sequence of G or C and A or T nucleotides are identical to the corresponding HCV fragment, which are mainly influencing secondary structure. This construct is coamplified and detected in the same reaction together with HCV target (Seq. ID No 10) in a non competitive manner using the primers and the probe mentioned in example 2 and 1, respectively.

Sequence of the cloned BglII/HindIII fragment of QS(pc) HCV (Seq. ID No 11):

SEQ New: 943 bp;

Composition 203 A; 287 C; 282 G; 171 T; 0 OTHER

Percentage: 22% A; 30% C; 30% G; 18% T; 0%OTHER

Molecular Weight(kDa): ssDNA: 291.24 dsDNA: 581.5

ORIGIN

```
         BglII
   1 AGATCTCCGC TGTGAGGTGG TATCTAGTGA GGGGACACTC CTTGATGACA GAAGTGCGTC
  61 TTTCGCAGAT CGGTACCGCA ATCATACTCA CAGCACGTCG GAGGTCCTGG GGGGGAGGGC
 121 CCTCTCGGTA TCACCAGACG CCTTGGCCAC TCATGTGGCC TTAACGGTCC TGCTGGCCCA
 181 GGAAAGAACC TAGTTGGGCG AGTTACGGAC CTCTAAACCC GCACGGGGGC GCTCTGACGA
```

```
241 TCGGCTCATC ACAACCCAGC GCTTTCCGGA ACACCATGAC GGACTATCCC ACGAACGCTC

301 ACGGGGCCCT CCAGAGCATC TGGCACGTGG TACTCGTGCT TAGGATTTGG AGTTTCTTTT

361 TGGTTTGCAT TGTGGTTGGC GGCAGGTGTC CTGCAGTTCA AGGGCCCGCC ACCAGTCTAG

421 CAACCACCTC AAATGGACAA CGGCGCGTCC CCGGGGTCCA ACCCACACGC GCGCGAGTCC

481 TTCTGAAGGC TCGCCAGCGT TGGAGCACCT TCCGCTGTTG GATAGGGGTT CCGAGCGGCT

541 GGGCTCCCGT CCCGGACCCG AGTCGGGCCC ATGGGAACCG GGGAGATACC GTTACTCCCG

601 TACCCCACCC GTCCTACCGA GGACAGTGGG GCACCAAGAG CCGGATCAAC CCCGGGGAGT

661 CTGGGGGCCG CATCCAGCGC ATTAAACCCA TTCCAGTAGC TATGGGAATG TACGCCGAAG

721 CGGCTGGAGT ACCCCATGTA AGGCGAGCAG CCGCGGGGAG ATCCCCCGCG GCGGTCCCGG

781 GACCGCGTAC CGCAGGCCCA AGACCTCCTG CCGCACTTGA TACGTTGTCC CTTAAACGGG

841 CCAACGAGAA AGAGATAGAA GGAGAACCCA AACGACAGAA CAAACTGGTA GGGTCGAAGG

901 CGAATACTTC ACGCGTAAAC ATGAGGATTA CCCATGTAAG CTT
                                          HindIII
```

Printed in bold: Amplicon (Seq. ID No 12) when using the Primers ST280pc and ST778pc for amplification.

Example 4

Comparison of Likely Formed Secondary Structures Formed by Single Stranded HCV Target Amplicon vs. Single Stranded Internal Control Amplicon and vs. a Scrambled Internal Control Amplicon QSHCV (Seq ID No 13).

Figure 4:
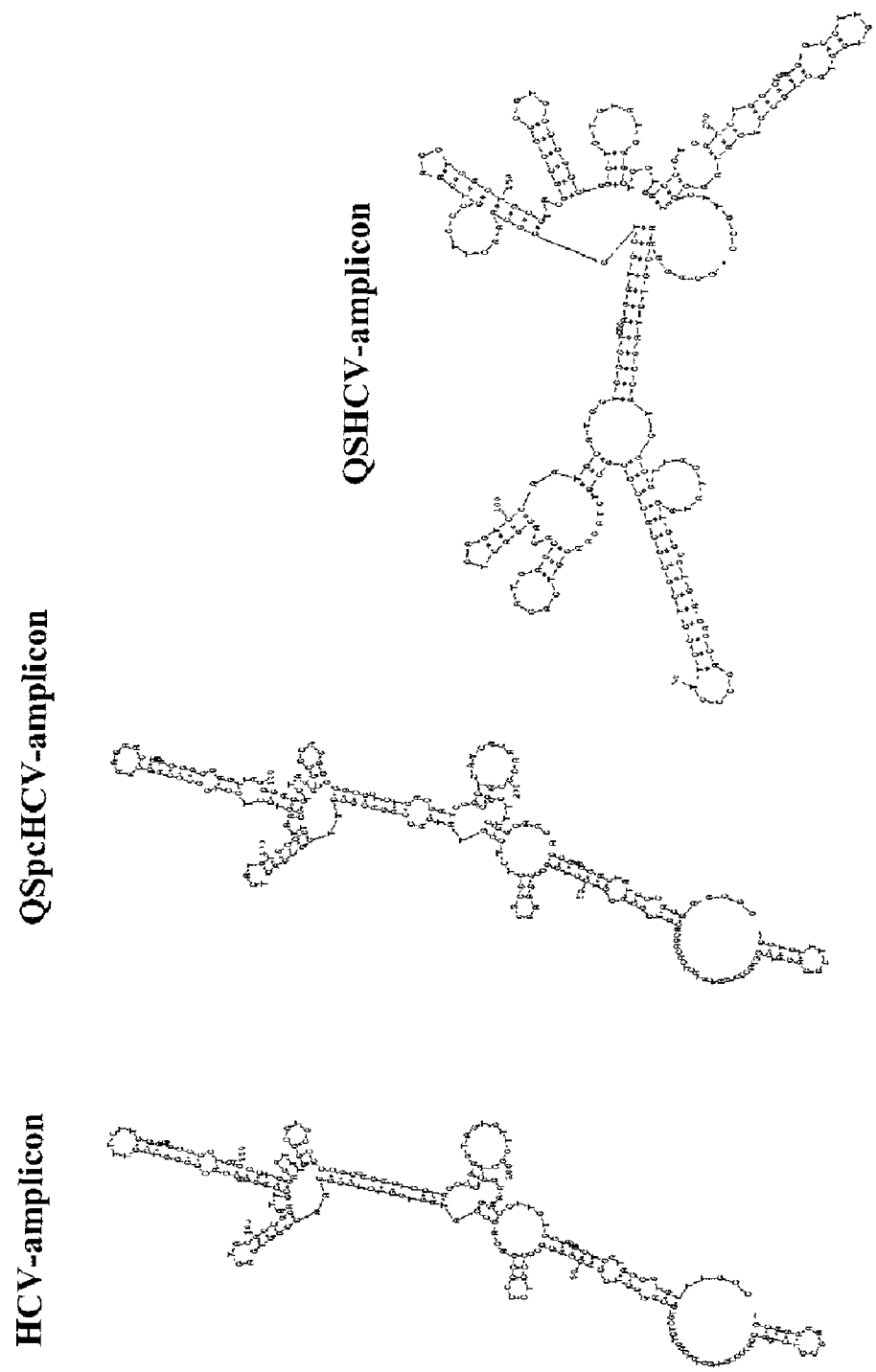
FIG. 4 shows the prediction of secondary structures done with Mfold version 3.0 for the HCV-amplicon, QS(pc)HCV-amplicon (parallel complementary to HCV-amplicon) and QSHCV-amplicon (control amplicon containing a scrambled nucleotide sequence, a ST2535 probe binding sequence, a ST280 and ST778 primer binding site and being of the same lenght as the HCV-amplicon).

The scrambled control nucleic acid (Seq ID No 13) has a ST280 and ST778 primer binding site, a ST2535 probe binding site and is of the same length as the HCV target amplicon and has the same GC-content. Folding was performed with Mfold version 3.0, see FIG. 4.

HCV- and the parallel complementary QS(pc)HCV amplicon have the potential to form similar secondary structures. This is different from the structure that is formed by the scrambled internal control (QSHCV) amplicon (Seq. ID No 13) that is state of the art. Since QS(pc)HCV amplicon (Seq. ID No 12) is a very close mimic of the HCV target amplicon, QS(pc)HCV (Seq. ID No 11) is the better choice to control target amplification.

Example 5

Cloning of an Internal Control for Competitive, Qualitative and Quantitative Nucleic Testing of HCV with Native Primer Binding Sites (ICSJ620HCV)

According to example 3 a synthetic 375 bpDNA fragment was cloned that is, besides the primer binding site, parallel complementary to HCV type I 5'UTR. The primer binding sites are identical to the target sequence to allow a competitive PCR between target and control. The sequence between both primers is parallel complementary in order to mimic the target. Since GC content, length and sequence of G/C and A/T between the primers is identical to the target, this construct is very close to the target amplicon. This construct can be coamplified and detected in the same reaction together with HCV target in a competitive manner using target amplification primers and the parallel complementary probe mentioned in example 1.

ICSJ620HCV (Seq. ID No 14)

SEQ New: 375 bp;

Composition 76 A; 104 C; 117 G; 78 T; 0 OTHER

Percentage: 20% A; 28% C; 31% G; 21% T; 0%OTHER

Molecular Weight (kDa): ssDNA: 116.05 dsDNA: 231.2

ORIGIN

```
  BglII
1 AGATCTCGGT CGGGGGACTA CCCCCGCTGT GAGGTGGTAC TTAGTGAGGG GACACTCCTT

61 GATGACAGAA GTGGCAGAAA GCGTCTAGCC ATGGCGTTAC ATACTCACAG CACGTCGGAG

121 GTCCTGGGGG GGAGGGCCCT CTCGGTATCA CCAGACGCCT TGGCCACTCA TGTGGCCTTA

181 ACGGTCCTGC TGGCCCAGGA AAGAACCTAG TTTGGGCGAG TTACGGACCT CTAAACCCGC

241 ACGGGGGCGC TCTGACGATC GGCTCATCAC AACCCAGCGC TTTCCGGTTG TGGTACTGCC

301 TGATAGGGTG CTTGCCTCGA GGGGCCCTCC AGAGCATCTG GCACGTGGAA ACATGAGGAT

361 TACCCATGTAAGCTT
              HindIII
```

Printed in bold: Amplicon (Seq. ID No 15) when using the primers ST280 and ST778 for amplification.

Example 6

Comparison of Annealing Curves Derived from HCV1b Wildtype, QSHCV and QS(pc)HCV

Related fragments of HCV-1b wildtype, QSHCV and QS(pc)HCV were amplified and subsequently amplification products were compared in an annealing experiments using SybrGreen as intercalating agent to get insight into folding kinetics of the amplicon

| | |
|---|---|
| 1000 IU | HCV-1b RNA, QSHCV or QS(pc)HCV in comparable concentrations (IU: International Unit, WHO-Standard) |
| 5% | DMSO |
| 5.64% | Glycerol |
| 50 mM | Tricine (pH = 8.3) |
| 100 mM | KOAc (pH = 7.5) |
| 300 µM | dNTP(A,C,G) |
| 50 µM | dTTP |
| 500 µM | dUTP |
| 20 pmol | NTQ21-46-A (Aptamer, Sequence: CGA TCA TCT CAG AAC ATT CTT AGC GTT TTG TTC TTG TGT ATG ATC G-PO$_4$) |
| 40 U | ZO5 Polymerase |
| 10 U | UNG (Uracil-N-Glycosylase) |
| 3 mM | Mn(Ac)$_2$ |
| 12 µl | Sybr-Green (1:300 dilution, from Molecular Probes, Leiden Netherlands; 10000× concentrated in DMSO) |
| ad 100 µl | water DEPC-treated |
| | Primers |

| Primers in amplification of HCV-1b and QSHCV |
|---|
| 15 pmol ST280 |
| 40 pmol ST778 |

| Primers in amplification of QS(pc)HCV |
|---|
| 15 pmol ST280pc |
| 40 pmol ST778pc |

The polymerase ZO5 is described in U.S. Pat. Nos. 5,455,170 and 5,674,738.

| Amplification cycles: |
|---|
| (50° C. 240 s |
| 59° C. 1800 s) 1x |
| (95° C. 15 s |
| 58° C. 25 s) 5x |
| (91° C. 15 s |
| 58° C. 25 s) 55x |

| Annealing curve |
|---|
| 0.5° C. steps beginning at 90° C. cooling to 70° C. |
| 20 s each step |

Amplification and annealing curves (detected by Sybr-Green intercalation) were done on an ABI Prism 7700 (Perkin Elmer Corp.)

Figure 5:
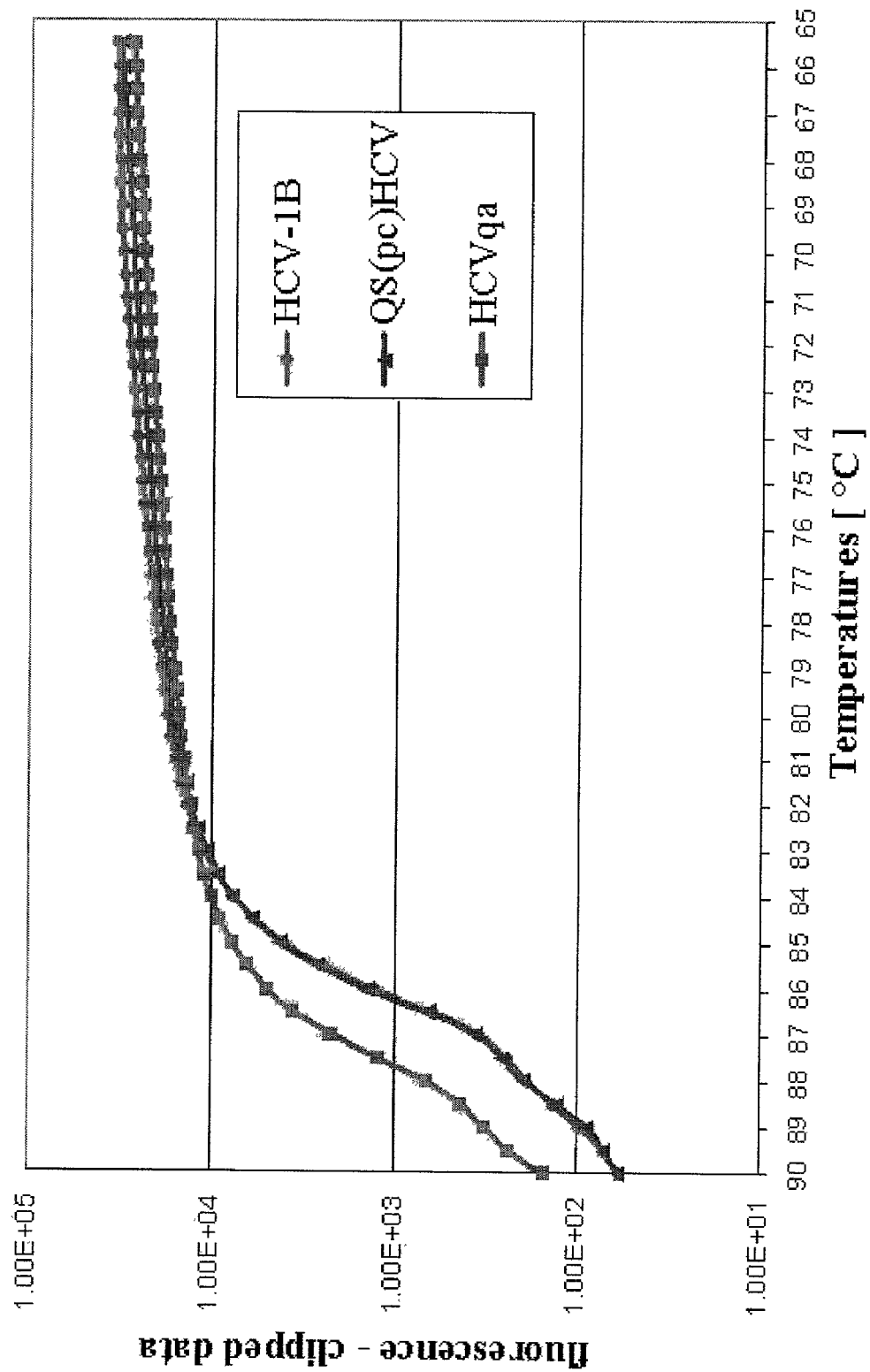
FIG. 5 shows the annealing curves of the amplified nucleic acid derived from the different internal standards QSHCV-amplificate (Seq. ID No. 14) and QS(pc)HCV amplificate (Seq. ID No. 13) compared with the HCV-1b amplificate

Comparison of annealing curves (see FIG. 5)

Reference in the assay is the annealing curve of the HCV-1b amplicon. The internal control construct that is used in the art QSHCV shows an annealing curve with a higher melting temperature, whereas the annealing curve of the parallel complementary control sequence QS(pc)HCV is matching the annealing curve of HCV-1b amplicon nearly perfectly.

The invention claimed is:

1. A composition comprising
    a target nucleic acid and a different control nucleic acid; and
    primers specific for target nucleic acid which amplify said target nucleic acid and primers specific for said control nucleic acid which amplify said control nucleic acid; and
    a control probe and a different target probe, wherein the control probe detects amplified control nucleic acid and the target probe detects amplified target nucleic acid, wherein at least one contiguous sequence of at least 8 nucleotides of the control probe is more than 80% parallel complementary to:
    at least 8 nucleotides of the target probe or
    at least 8 nucleotides complementary to the target probe.

2. The composition of claim 1, wherein said target nucleic acid comprises a primer binding site and said control nucleic acid comprises a sequence that is parallel complementary to the primer binding site of said target nucleic acid or to the complementary strand of said target nucleic acid.

3. The composition of claim 1, wherein said target nucleic acid comprises a probe binding site and said control nucleic acid comprises a sequence that is parallel complementary to the probe binding site of said target nucleic acid or the complementary strand of the probe binding site of said target nucleic acid.

4. The composition of claim 1, wherein the target nucleic acid is a DNA molecule.

5. The composition of claim 1, wherein the target nucleic acid is an RNA molecule.

6. The composition of claim 1, wherein said control nucleic acid comprises at least one contiguous sequence of at least 10 nucleotides in length essentially parallel complementary to said target nucleic acid region or to the complementary strand of said target nucleic acid region.

7. The composition of claim 1, further comprising a thermostable DNA polymerase.

8. A kit for the amplification of a target nucleic acid comprising:
    an instruction manual;
    a target nucleic acid and a different control nucleic acid; and
    primers specific for said target nucleic acid which amplify said target nucleic acid and primers specific for said control nucleic acid which amplify said control nucleic acid; and
    a control probe and a different target probe, wherein the control probe detects amplified control nucleic acid and the target probe detects amplified target nucleic acid, wherein at least one contiguous sequence of at least 8 nucleotides of the control probe is more than 80% parallel complementary to:
    at least 8 nucleotides of the target probe or
    at least 8 nucleotides complementary to the target probe.

9. The kit of claim 8, wherein the target nucleic acid is a DNA molecule.

10. The kit of claim 8, wherein the target nucleic acid is an RNA molecule.

11. The kit of claim 8, wherein said control nucleic acid comprises at least one contiguous sequence of at least 10 nucleotides in length essentially parallel complementary to said target nucleic acid region or to the complementary strand of said target nucleic acid region.

12. The kit of claim 8, further comprising a thermostable DNA polymerase.

13. The kit of claim 8, wherein said target nucleic acid comprises a primer binding site and said control nucleic acid comprises a sequence that is parallel complementary to the primer binding site of said target nucleic acid or to the complementary strand of said target nucleic acid.

14. The kit of claim 8, wherein said target nucleic acid comprises a probe binding site and said control nucleic acid comprises a sequence that is parallel complementary to the probe binding site of said target nucleic acid or the complementary strand of the probe binding site of said target nucleic acid.

* * * * *

SEQUENCE LISTING

<160> NUMBER OF SEQ ID NOS: 17

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Artificial
      sequence to exemplify principle

<400> SEQUENCE: 1
agcgcatgcc agattactgg c                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Artificial
      sequence to exemplify principle

<400> SEQUENCE: 2
tcgcgtacgg tctaatgacc g                                              21

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: ST650 HCV
      specific probe sequence

<400> SEQUENCE: 3
cggtgtactc accgttccg cagaccacta tggc                                    33

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Sequence
      ST2535 probe sequence

<400> SEQUENCE: 4
tggactcagt ccttggtca tctcaccttc t                                       30

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: ST650pc
      probe seqeunce (parallel-complementary to ST650)

<400> SEQUENCE: 5
gccacatgag tggcaaggc gtctggtgat accg                                    33

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: sequence
      ST280 HCV-specific primer sequence

<400> SEQUENCE: 6
gcagaaagcg tctagccatg gcgtta                                            26

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence:  ST778
      HCV-specific primer sequence

<400> SEQUENCE: 7
gcaagcaccc tatcaggcag taccacaa                                          28

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:  ST280pc
      primer parallel complement to ST280

<400> SEQUENCE: 8
cgtctttcgc agatcggtac ctcaat                                            26

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: ST778pc
      primer parallel-complement to ST778

<400> SEQUENCE: 9
cgttcgtggg atagtccgtc atggtgtt                                         28

<210> SEQ ID NO 10
<211> LENGTH: 241
<212> TYPE: DNA
<213> ORGANISM: Artificial Sequence
<220> FEATURE:
<223> OTHER INFORMATION: Description of Artificial Sequence: DNA
      sequence derived by amplification of HCV type 1 using primers
      ST280 and ST778

<400> SEQUENCE: 10
gcagaaagcg tctagccatg gcgttagtat gagtgtcgtg cagcctccag gaccccccct     60
cccgggagag ccatagtggt ctgcggaacc ggtgagtaca ccggaattgc caggacgacc    120
gggtcctttc ttggatcaac ccgctcaatg cctggagatt tgggcgtgcc cccgcgagac    180
tgctagccga gtagtgttgg gtcgcgaaag gccttgtggt actgcctgat agggtgcttg    240
c                                                                    241

<210> SEQ ID NO 11
<211> LENGTH: 943
<212> TYPE: DNA
<213> ORGANISM: Artificial Sequence
<220> FEATURE:
<223> OTHER INFORMATION: Description of Artificial Sequence: QS (pc) HCV
      being parallel-complement to according region of HCV type 1 genome

<400> SEQUENCE: 11
agatctccgc tgtgaggtgg tatctagtga ggggacactc cttgatgaca gaagtgcgtc     60
tttcgcagat cggtaccgca atcatactca cagcacgtcg gaggtcctgg gggggagggc    120
cctctcggta tcaccagacg ccttggccac tcatgtggcc ttaacggtcc tgctggccca    180
ggaaagaacc tagttgggcg agttacggac ctctaaaccc gcacggggc gctctgacga     240 tcggctcatc acaacccagc gctttccgga acaccatgac ggactatccc acgaacgctc    300
acggggccct ccagagcatc tggcacgtgg tactcgtgct taggatttgg agtttctttt    360
tggtttgcat tgtggttggc ggcaggtgtc ctgcagttca agggcccgcc accagtctag    420
caaccacctc aaatggacaa cggcgcgtcc cgggggtcca acccacacgc gcgcgagtcc    480
ttctgaaggc tcgccagcgt tggagcacct tccgctgttg datagggtt ccgagcggct    540 gggctcccgt cccggacccg agtcgggccc atggaaccg ggagatacc gttactcccg     600 taccccaccc gtcctaccga ggacagtggg gcaccaagag ccggatcaac cccggggagt    660 ctggggccg catccagcgc attaaaccca ttccagtagc tatgggaatg tacgccgaag    720
cggctggagt accccatgta aggcgagcag ccgcggggag atccccgcg gcggtcccgg    780 gaccgcgtac cgcaggccca agacctcctg ccgcacttga tacgttgtcc cttaaacggg    840
ccaacgagaa agagatagaa ggagaaccca aacgacagaa caaactggta gggtcgaagg    900
cgaatacttc acgcgtaaac atgaggatta cccatgtaag ctt                      943

<210> SEQ ID NO 12
<211> LENGTH: 241
<212> TYPE: DNA
<213> ORGANISM: Artificial Sequence
<220> FEATURE:
<223> OTHER INFORMATION: Description of Artificial Sequence: Amplicon
      derived from QS (pc)HCV using the primers ST280pc and ST778pc

<400> SEQUENCE: 12
cgtctttcgc agatcggtac cgcaatcata ctcacagcac gtcggaggtc ctggggggga     60
gggccctctc ggtatcacca gacgccttgg ccactcatgt ggccttaacg gtcctgctgg    120
cccaggaaag aacctagttg gcgagttac ggacctctaa acccgcacgg gggcgctctg    180
acgatcggct catcacaacc cagcgctttc cggaacacca tgacggacta tcccacgaac    240
g                                                                   241

<210> SEQ ID NO 13
<211> LENGTH: 241
<212> TYPE: DNA
<213> ORGANISM: Artificial Sequence
<220> FEATURE:
<223> OTHER INFORMATION: Description of artificial sequence: Amplicon
      sequence derived from QS HCV (HCV amplification control having
      binding sites for ST280, ST778, and ST2535) using primers ST280 and
      ST778

<400> SEQUENCE: 13
gcagaaagcg tctagccatg gcgttagtat agtggcgtga gagcagccct tgcctcgccc     60
accgcgcgtc tagaaggtga gatgaccaga ggactgagtc caatgcatgc tggctccgag    120
atgctccgca aacttgccgt caacgtgact gcgtacggcg ggcgtgcccg cctggctgtg    180
tatgagctgg tgaccgtgat ctggctggag gccttgtggt actgcctgat agggtgcttg    240
c                                                                   241

<210> SEQ ID NO 14
<211> LENGTH: 375
<212> TYPE: DNA
<213> ORGANISM: Artificial Sequence
<220> FEATURE:
<223> OTHER INFORMATION: Description of Artificial Sequence: ICSJ620 HCV
      (HCV specific amplification control having a binding site for ST280
      and ST778 and an internal region being parallel-complement to HCV)

<400> SEQUENCE: 14
agatctcggt cggggagacta ccccgctgt gaggtggtac ttagtgaggg gacactcctt     60
gatgacagaa gtggcagaaa gcgtctagcc atggcgttac atactcacag cacgtcggag    120
gtcctggggg ggagggccct ctcggtatca ccagacgcct tggccactca tgtggcctta    180
acggtcctgc tggcccagga aagaacctag tttgggcgag ttacggacct ctaaacccgc    240 acggggcgc tctgacgatc ggctcatcac aacccagcgc tttccggttg tggtactgcc    300
tgatagggtg cttgcctcga ggggccctcc agagcatctg gcacgtggaa acatgaggat    360
tacccatgta agctt                                                    375

<210> SEQ ID NO 15
<211> LENGTH: 242
<212> TYPE: DNA
<213> ORGANISM: Artificial Sequence
<220> FEATURE:
<223> OTHER INFORMATION: Description of artificial sequence: Amplicon
      derived from ICSJ620 HCV (HCV-specific amplification control) using
      ST280 and ST778 as primers -continued

```
<400> SEQUENCE: 15
gcagaaagcg tctagccatg gcgttacata ctcacagcac gtcggaggtc ctgggggga      60 gggccctctc ggtatcacca gacgccttgg ccactcatgt ggccttaacg gtcctgctgg    120
cccaggaaag aacctagttt gggcgagtta cggacctcta aacccgcacg ggggcgctct    180
gacgatcggc tcatcacaac ccagcgcttt ccggttgtgg tactgcctga tagggtgctt    240
gc                                                                   242

<210> SEQ ID NO 16
<211> LENGTH: 46
<212> TYPE: DNA
<213> ORGANISM: Artificial Sequence
<220> FEATURE:
<223> OTHER INFORMATION: Description of Artificial Sequence:  NTQ21-46-A
      aptamer sequence

<400> SEQUENCE: 16
cgatcatctc agaacattct tagcgttttg ttcttgtgta tgatcg                    46

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence:  Sequence
      to exemplify principle

<400> SEQUENCE: 17
cggtcattag accgtacgcg a                                               21
```